(12) United States Patent
Yamamoto et al.

(10) Patent No.: US 9,952,210 B2
(45) Date of Patent: Apr. 24, 2018

(54) MICROCHIP SOLUTION SENDING SYSTEM

(75) Inventors: Noriaki Yamamoto, Machida (JP); Youichi Aoki, Fuchu (JP)

(73) Assignee: KONICA MINOLTA, INC., Tokyo (JP)

( * ) Notice: Subject to any disclaimer, the term of this patent is extended or adjusted under 35 U.S.C. 154(b) by 272 days.

(21) Appl. No.: 14/116,219

(22) PCT Filed: May 8, 2012

(86) PCT No.: PCT/JP2012/061718
§ 371 (c)(1),
(2), (4) Date: Nov. 7, 2013

(87) PCT Pub. No.: WO2012/153723
PCT Pub. Date: Nov. 15, 2012

(65) Prior Publication Data
US 2014/0099236 A1  Apr. 10, 2014

(30) Foreign Application Priority Data
May 9, 2011  (JP) .................................. 2011-104153

(51) Int. Cl.
*B01L 3/00* (2006.01)
*G01N 33/543* (2006.01)
*G01N 35/10* (2006.01)

(52) U.S. Cl.
CPC .. *G01N 33/54373* (2013.01); *B01L 3/502715* (2013.01); *B01L 2200/0605* (2013.01);
(Continued)

(58) Field of Classification Search
None
See application file for complete search history.

(56) References Cited

U.S. PATENT DOCUMENTS 7,135,330 B2   11/2006 Ohtaka
8,178,305 B2   5/2012 Kohara et al.
(Continued)

FOREIGN PATENT DOCUMENTS

JP  09-015115 A   1/1997
JP  2005-134372 A  5/2005
(Continued)

OTHER PUBLICATIONS

Extended European Search Report issued in connection with the corresponding application No. 12782044.7-1553/2708901, PCT/JP2012061718; dated Oct. 2, 2014.
(Continued)

*Primary Examiner* — Rebecca L Martinez
(74) *Attorney, Agent, or Firm* — Cantor Colburn LLP

(57) ABSTRACT

A microchip solution sending system may include a flow passage assembly that is at least provided with a fine flow passage that is provided with a detection region including a formed reaction field to which an antibody that reacts with a specific antigen is fixed; and a micro pump that is connected to the flow passage assembly and that is configured to send a specimen material solution that includes the specific antigen in a reciprocating manner. The specimen material solution that has been sent may pass through the detection region in a repetitive manner in the case in which the micro pump sends the specimen material solution in a reciprocating manner.

2 Claims, 14 Drawing Sheets

(52) U.S. Cl.
CPC .............. *B01L 2300/0877* (2013.01); *B01L 2400/0487* (2013.01); *G01N 2035/106* (2013.01)

(56) References Cited

U.S. PATENT DOCUMENTS

| | | |
|---|---|---|
| 2004/0028559 A1 | 2/2004 | Schuck |
| 2007/0036679 A1* | 2/2007 | Munenaka .................. 422/68.1 |
| 2010/0184238 A1 | 7/2010 | Sandhu |
| 2012/0156800 A1 | 6/2012 | Aoki et al. |

FOREIGN PATENT DOCUMENTS

| | | |
|---|---|---|
| JP | 2006-90985 A | 4/2006 |
| JP | 2008228735 A | 10/2008 |
| JP | 2009270923 A | 11/2009 |
| JP | 2010243419 A | 10/2010 |
| JP | 2011080035 A | 4/2011 |
| WO | 2006123459 A1 | 11/2006 |
| WO | 2010013334 A1 | 2/2010 |
| WO | 2011027851 A1 | 3/2011 |

OTHER PUBLICATIONS

International Search Report for International Application No. PCT/JP2012/061716; dated Jun. 12, 2012, with English Translation.
Writen Opinion of the International Searching Authority for International Application No. PCT/JP2012/061718, dated Jun. 12, 2012, with English translation.
European Office Action corresponding to Application No. 12782044.7-1553; dated Dec. 20, 2017.

* cited by examiner

[Fig. 1]
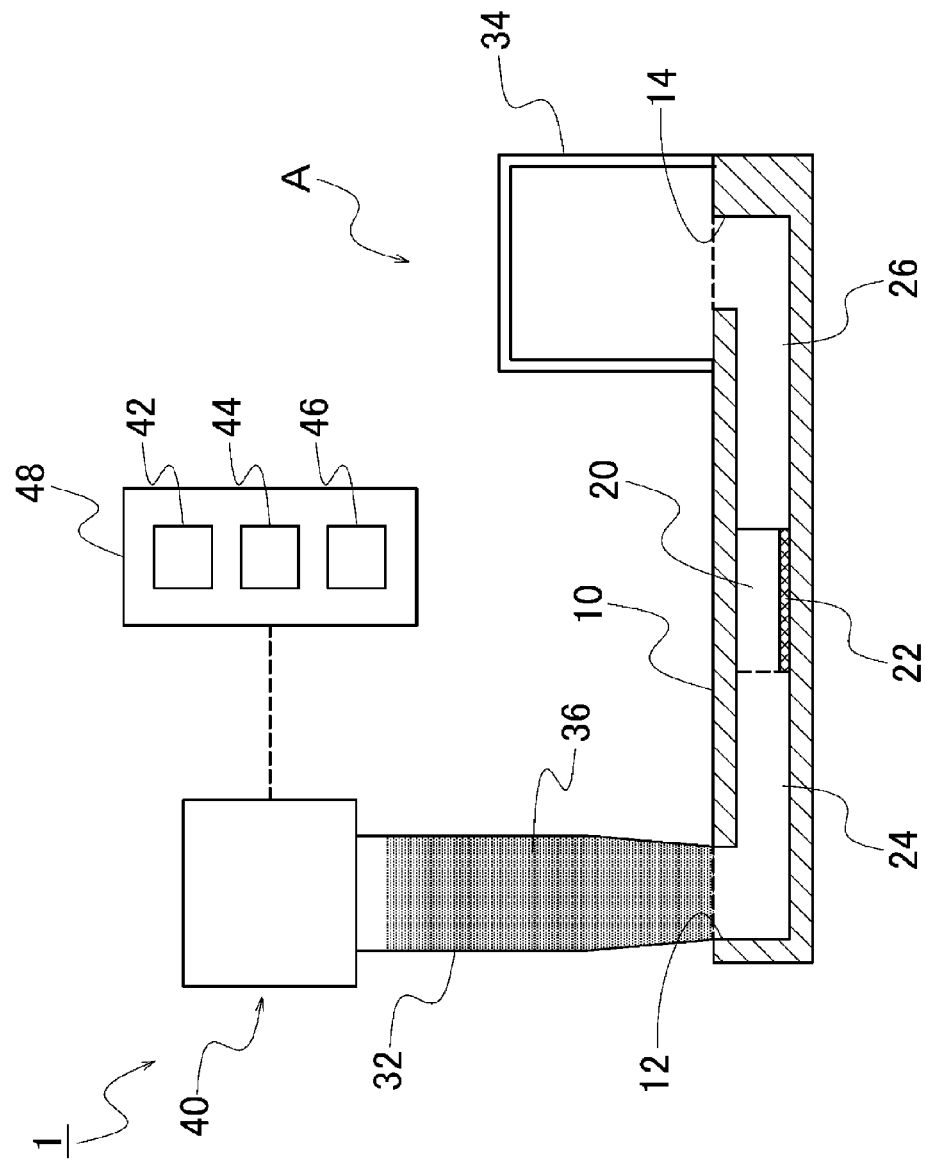

[Fig. 2]
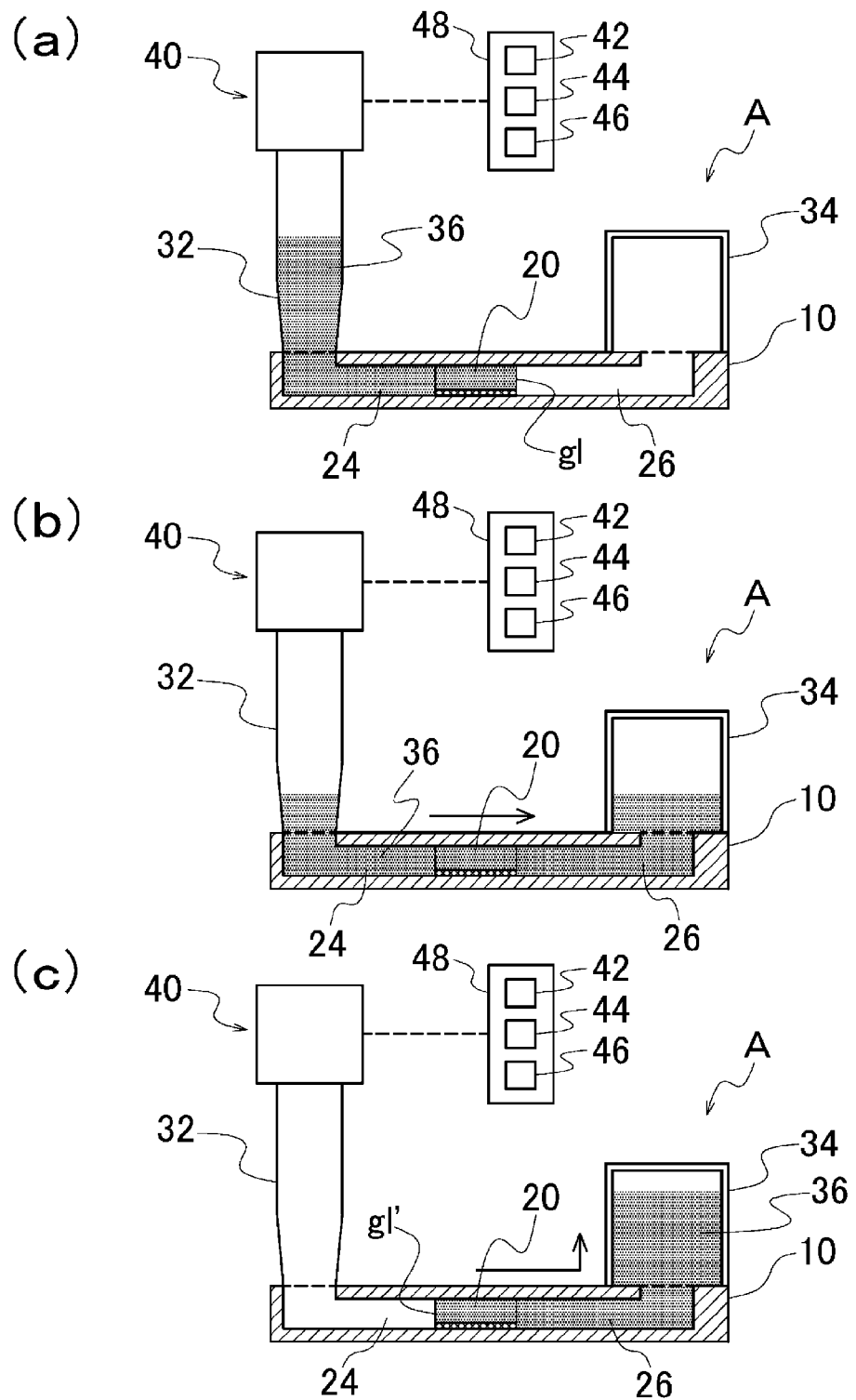

[Fig. 3]
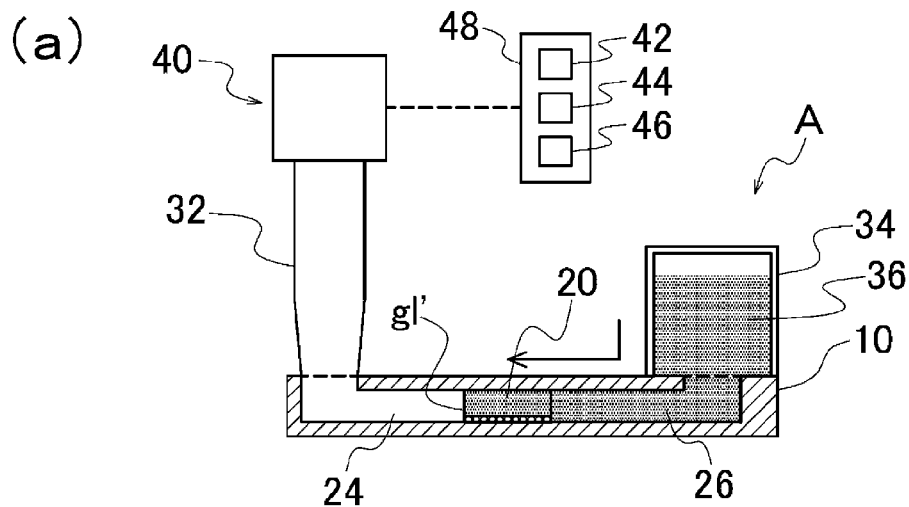
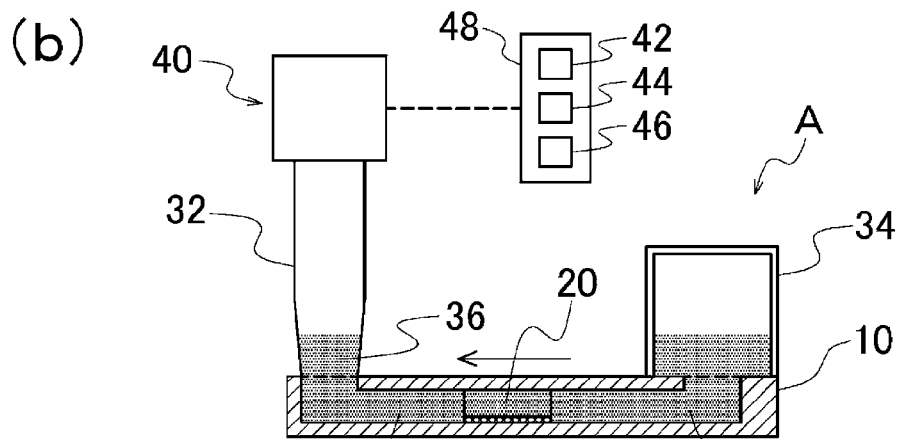
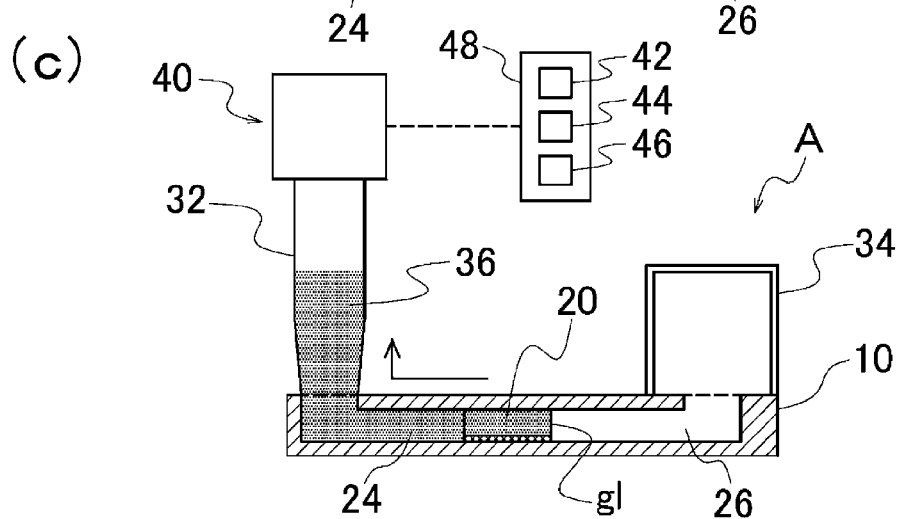

[Fig. 4]
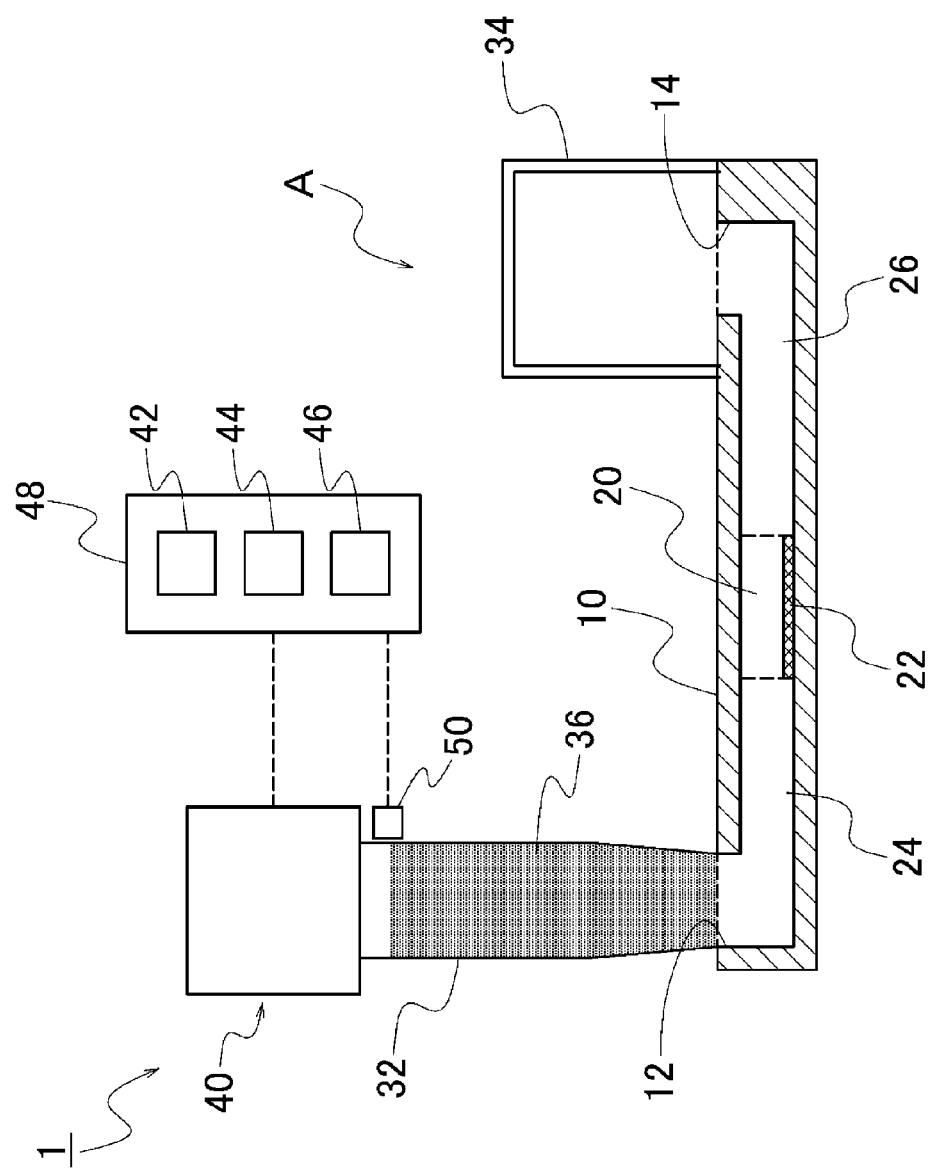

[Fig. 5]
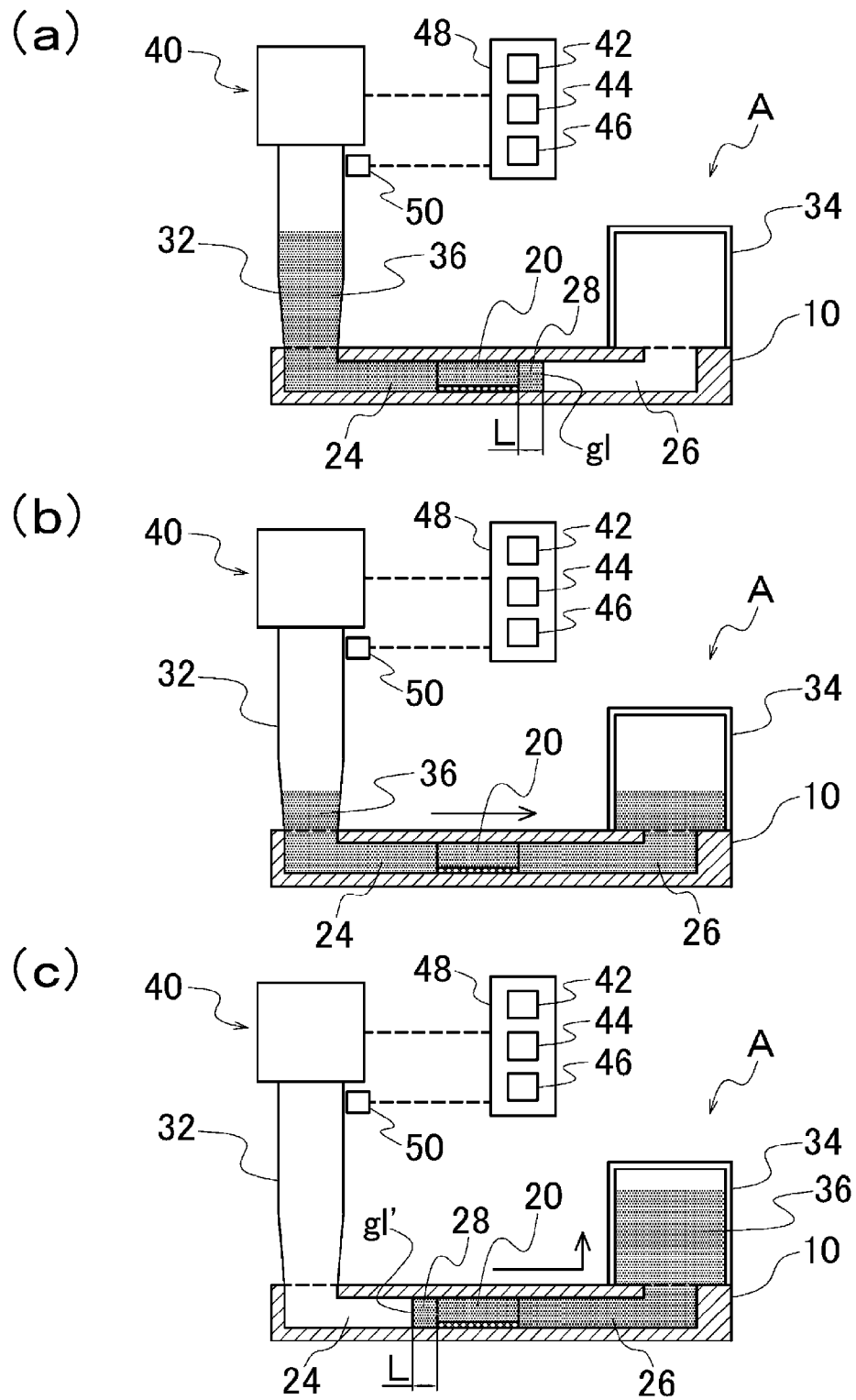

[Fig. 6]
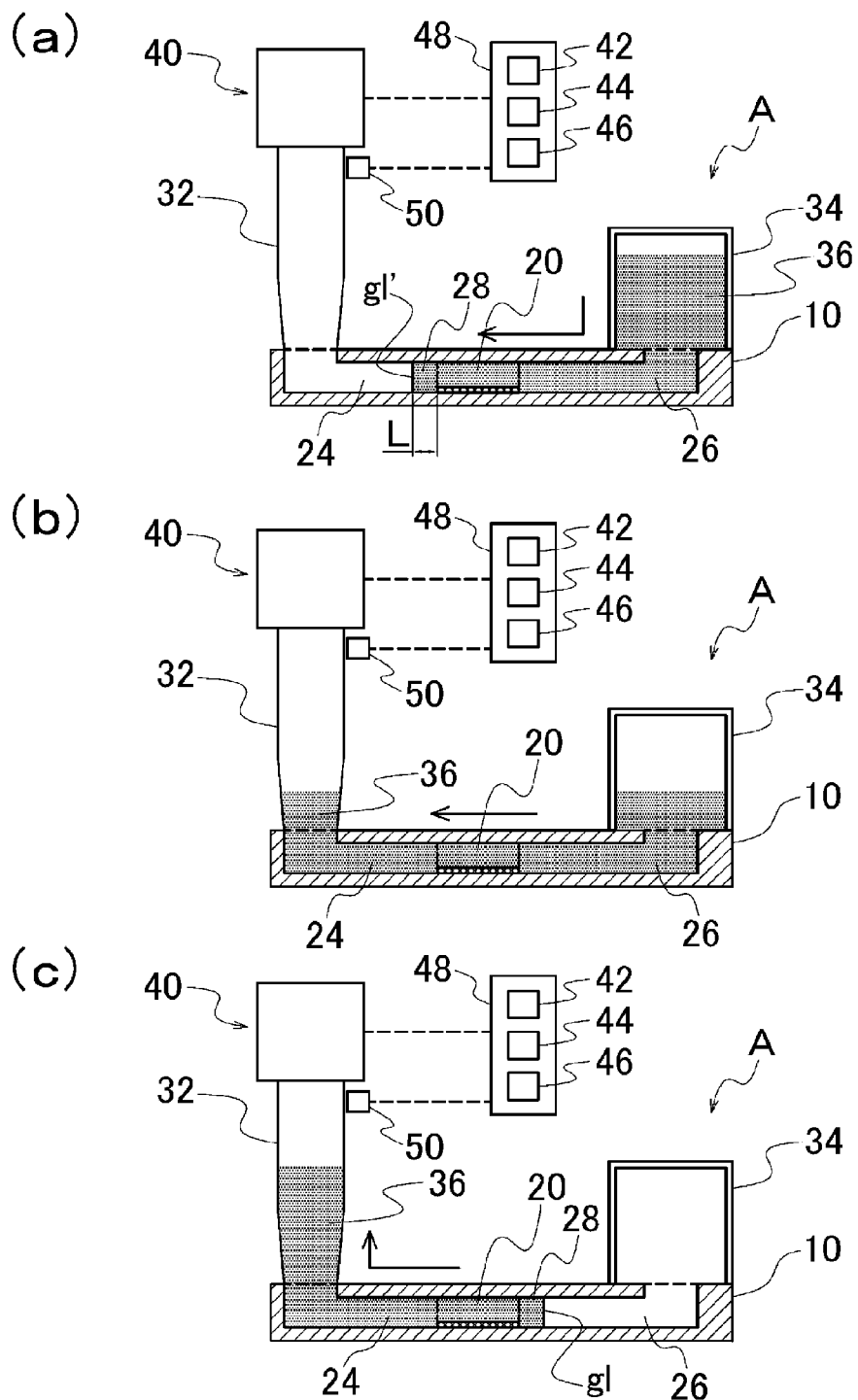

[Fig. 7]
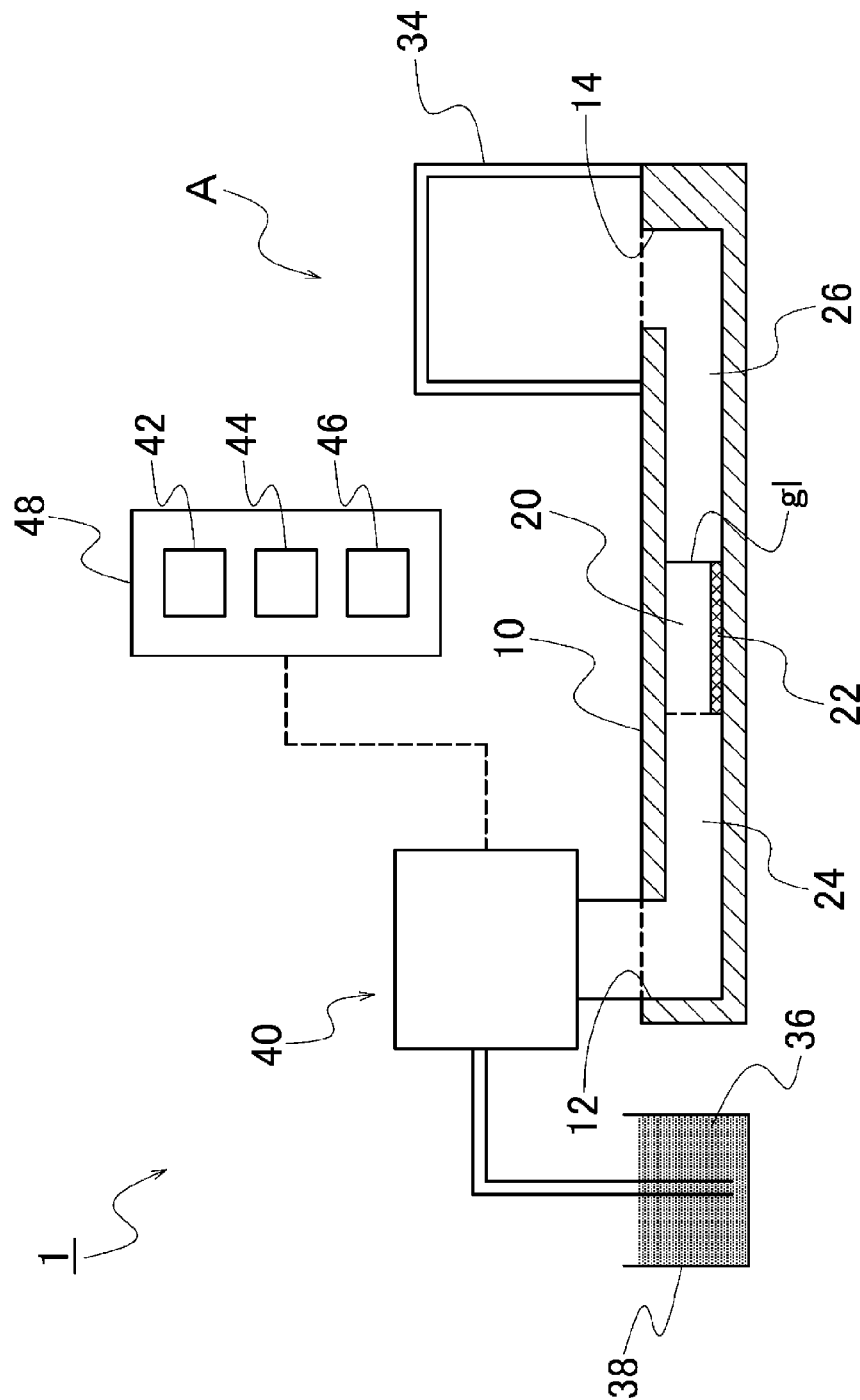

[Fig. 8]
(a)
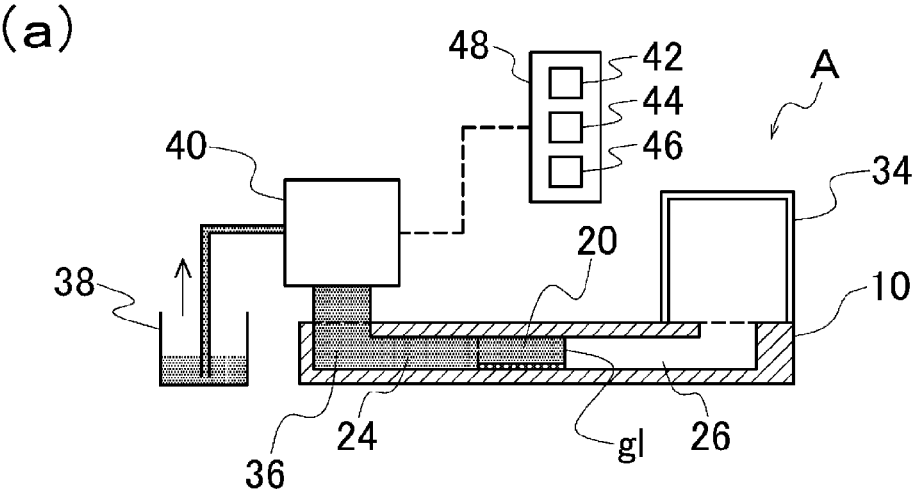
(b)
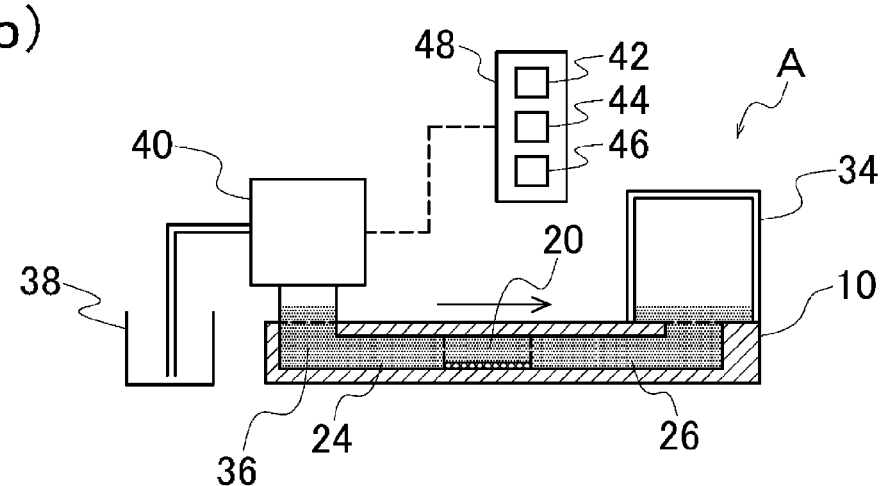
(c)
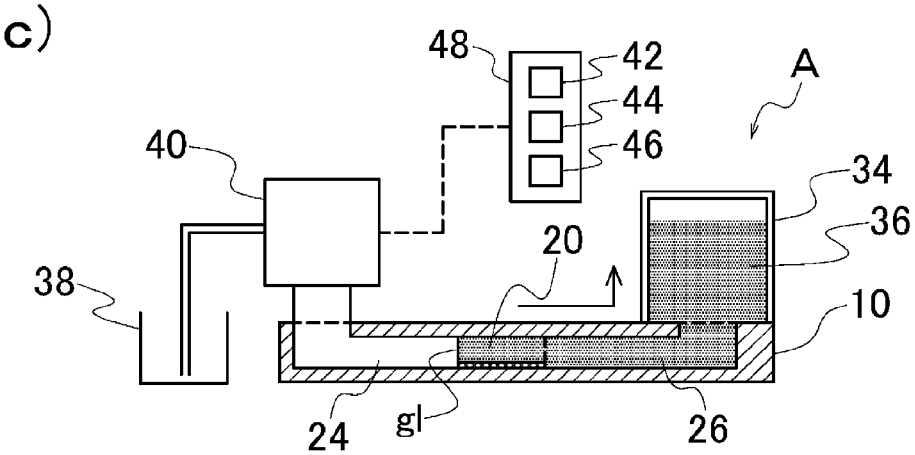

[Fig. 9]
(a)
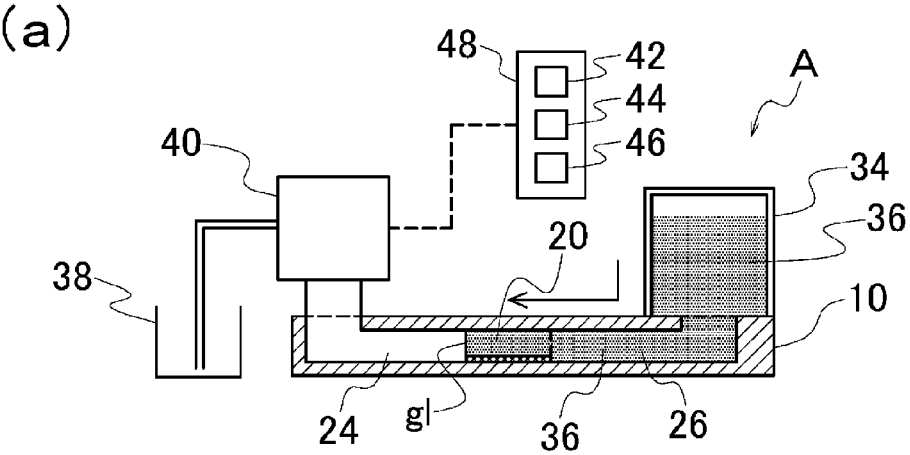
(b)
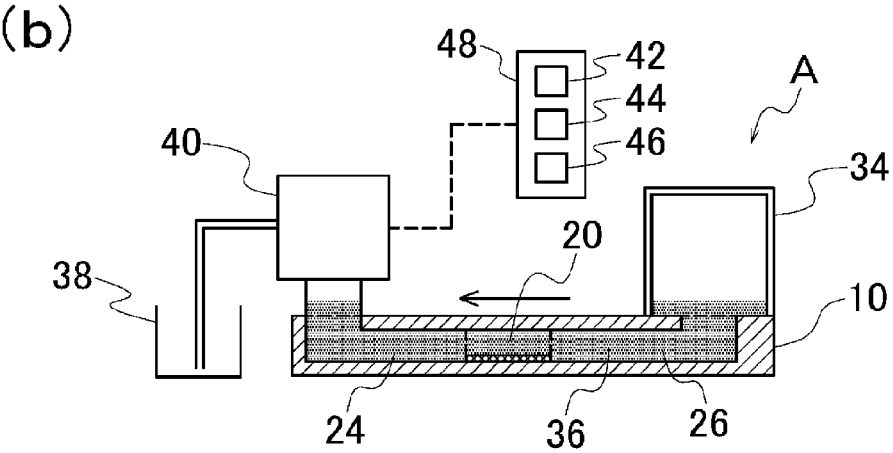
(c)
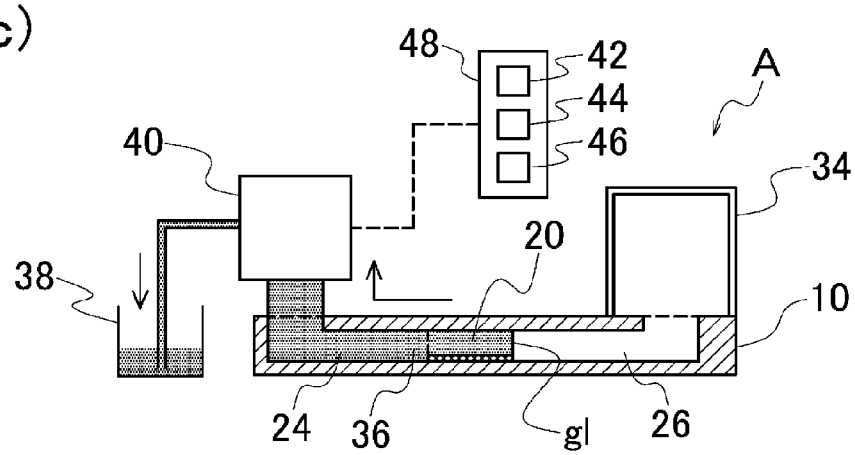

[Fig. 10]
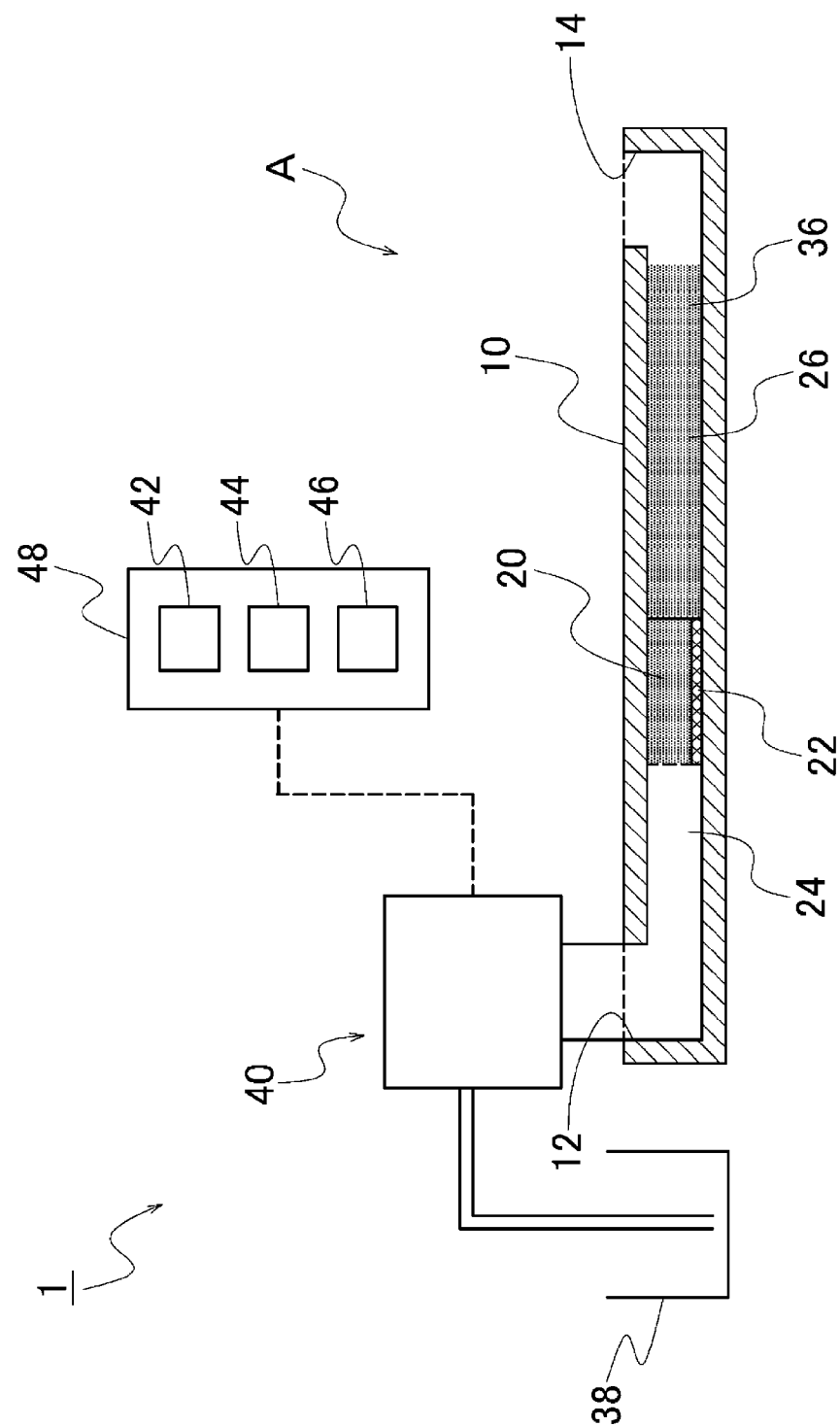

[Fig. 11]
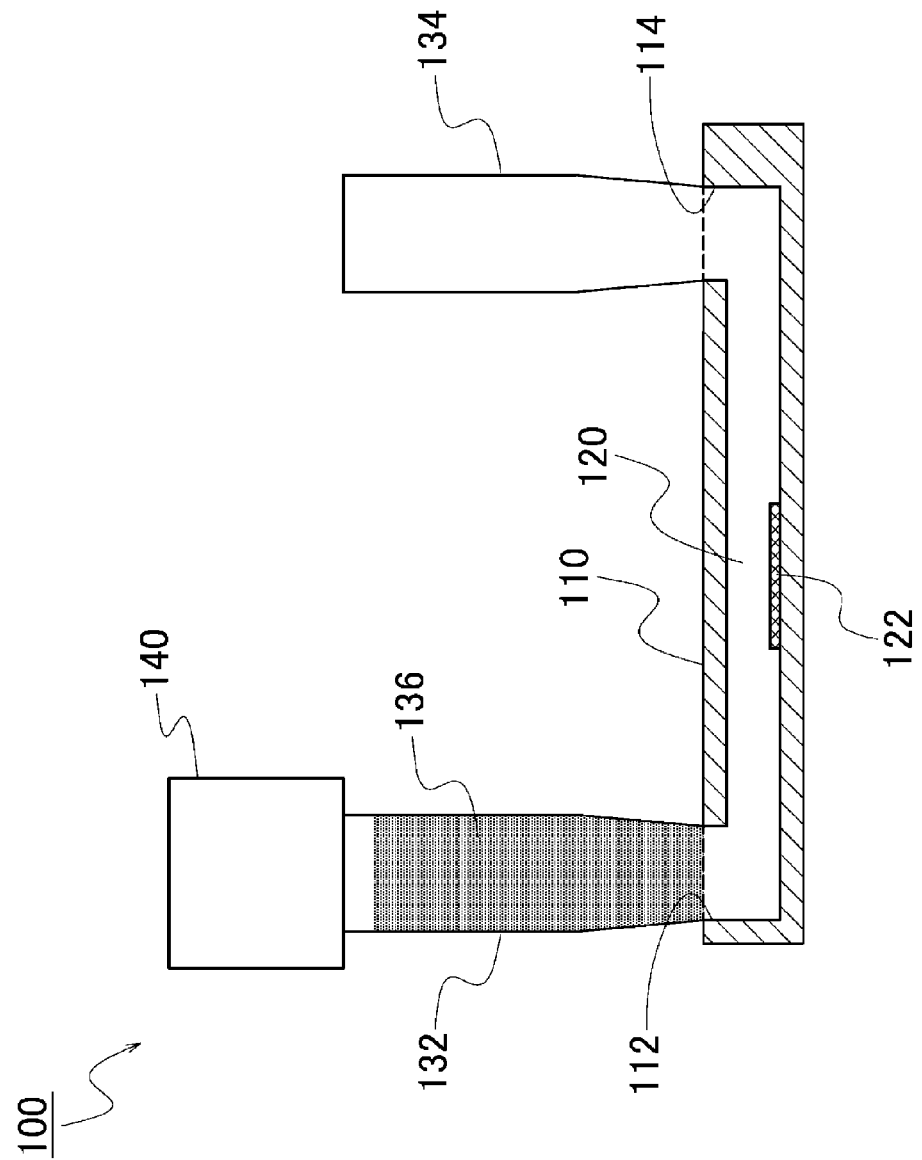

[Fig. 12]
(a)
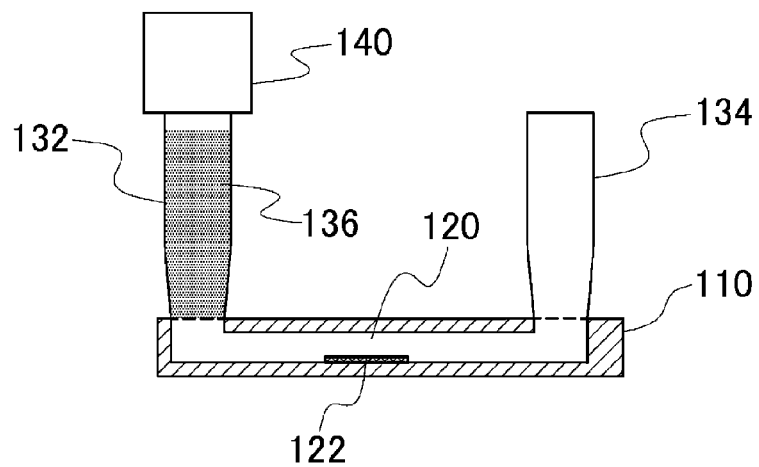
(b)
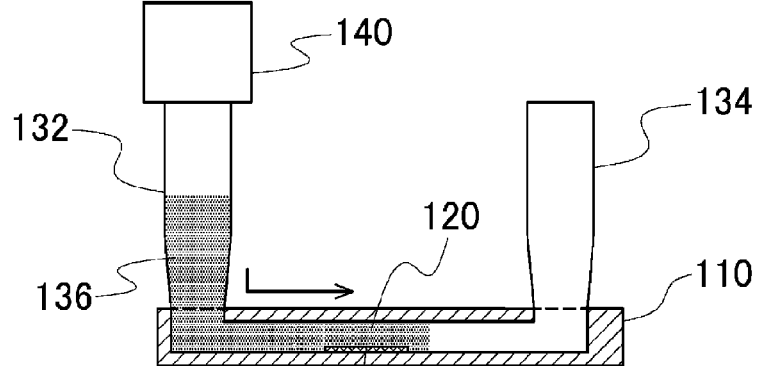
(c)
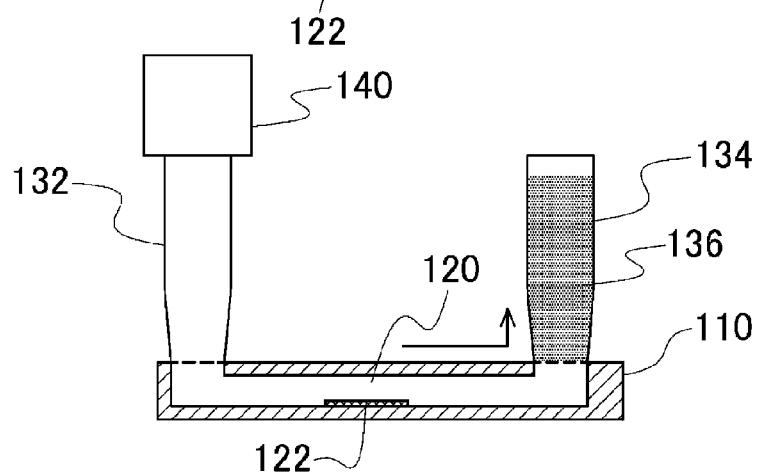

[Fig. 13]
(a)
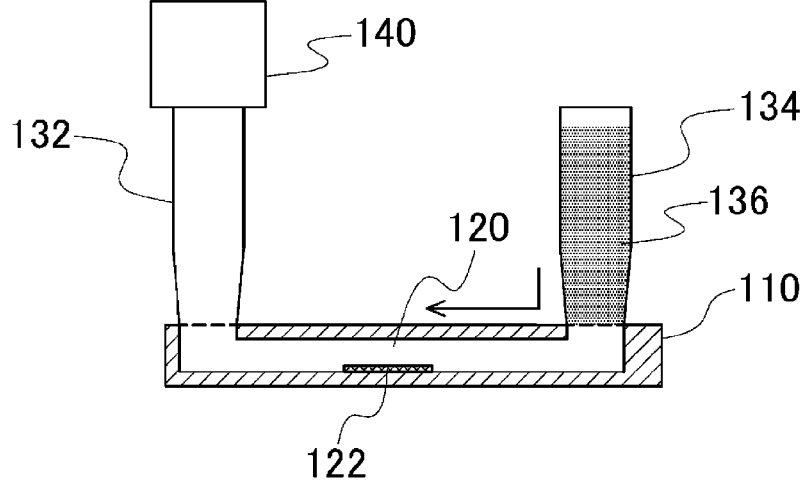
(b)
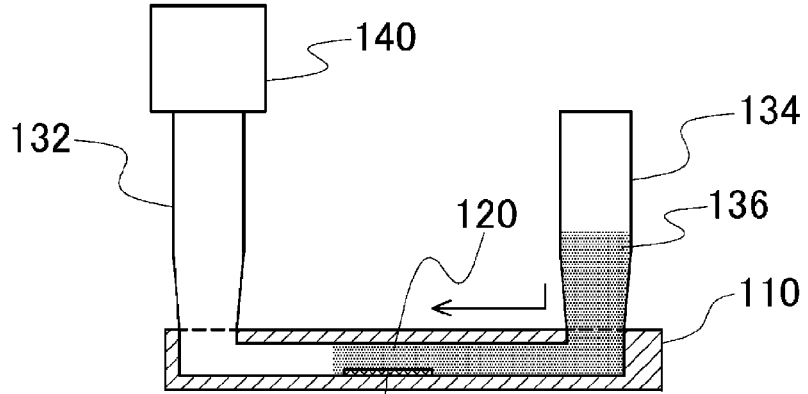
(c)
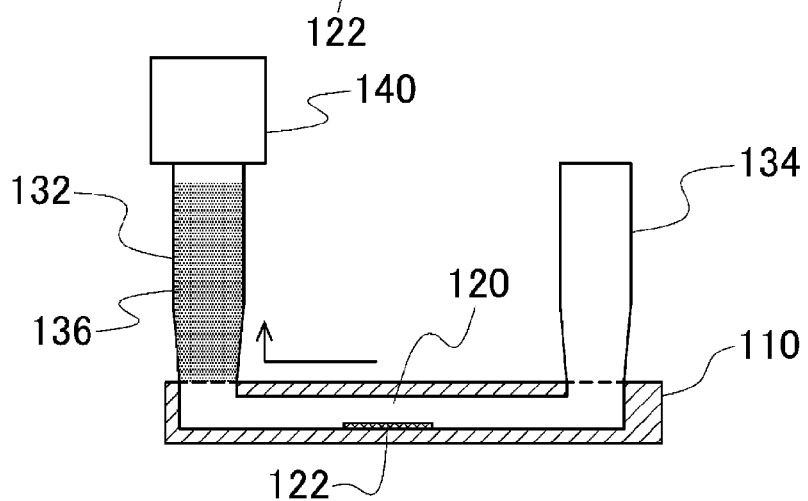

[Fig. 14]
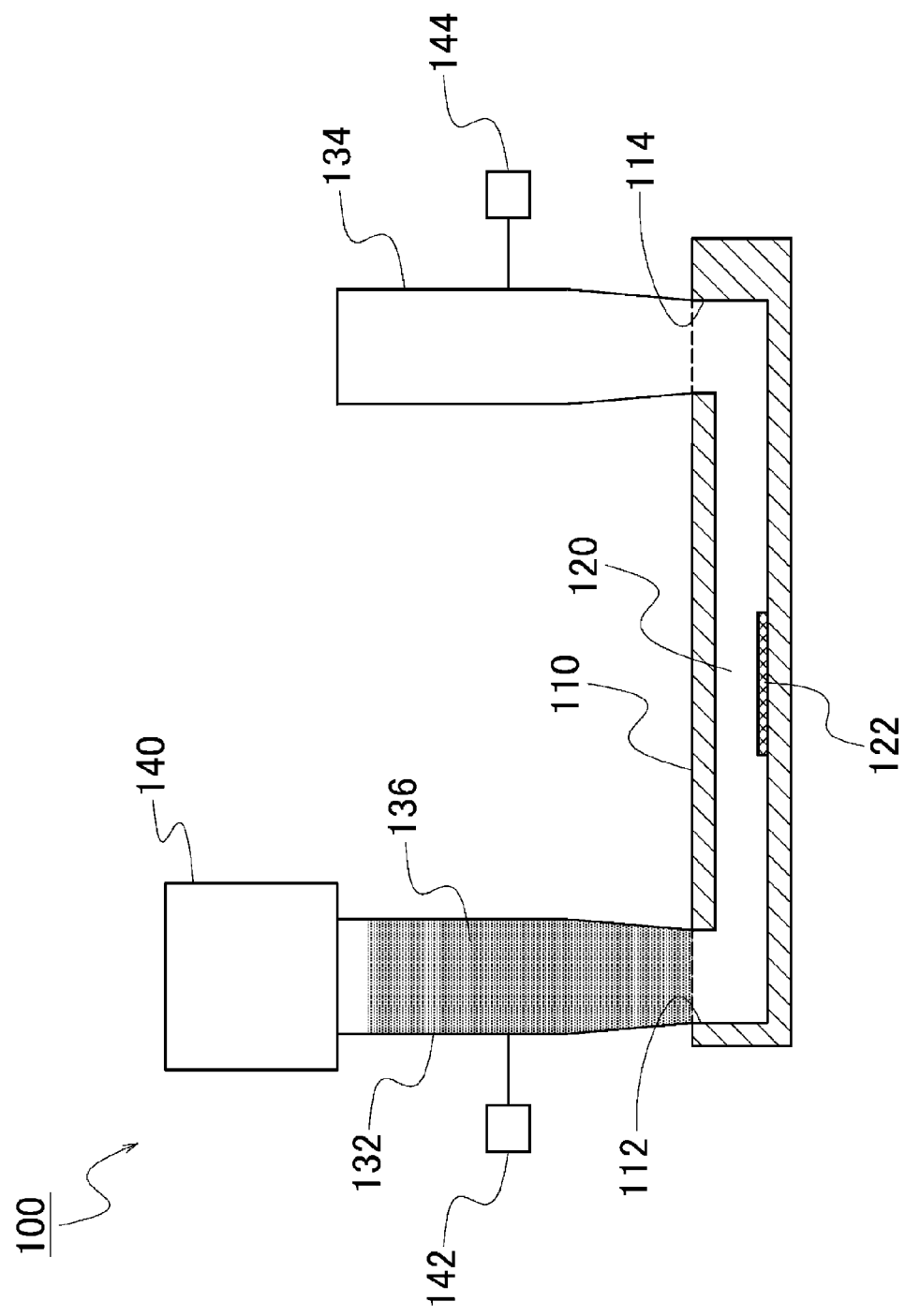

MICROCHIP SOLUTION SENDING SYSTEM

This is the U.S. national stage of application No. PCT/JP2012/061718, filed on 8 May 2012. Priority under 35 U.S.C. § 119(a) and 35 U.S.C. § 365(b) is claimed from Japanese Application No. 2011-104153, filed 9 May 2011, the disclosure of which is also incorporated herein by reference.

TECHNICAL FIELD

The present invention relates to a microchip solution sending system. More specifically, the present invention relates to a microchip solution sending system that is suitably utilized for an inspection and an analysis of a biological substance in which an antigen antibody reaction is used.

BACKGROUND ART

In the case in which a detection of an extremely fine substance is carried out, a wide variety of specimen material detection apparatus has been used for enabling an inspection of such a substance by putting a physical phenomenon of a substance to practical use from the past.

As one of such specimen material detection apparatuses, there can be mentioned for instance a surface plasmon resonance apparatus (hereafter referred to as an SPR apparatus) in which a phenomenon for obtaining a high optical output by a resonance of an electron and a light in a minute region of a nanometer level or the like (a surface plasmon resonance (SPR: Surface Plasmon Resonance) phenomenon is put to practical use and an extremely fine analyte in a biological body is detected for instance.

As one of such specimen material detection apparatuses, there also can be mentioned for instance a surface plasmon-field enhanced fluorescence spectroscopic measurement apparatus (hereafter referred to as an SPFS apparatus) in which the analyte detection can be carried out with a higher degree of accuracy as compared with the SPR apparatus based on a principle of a surface plasmon-field enhanced fluorescence spectroscopy (SPFS: Surface Plasmon-field enhanced Fluorescence Spectroscopy) for putting a surface plasmon resonance (SPR) phenomenon to practical use.

For the above described specimen material detection apparatus, a specimen material solution that contains an analyte (antigen) that is a detection target is prepared in advance, the specimen material solution is sent to a fine flow passage, and an analyte (antigen) is captured with an antibody that is fixed to a reaction field that is disposed in the fine flow passage. The specimen material detection apparatus is provided with a microchip solution sending system for sending a specimen material solution into a fine flow passage most commonly.

As such a microchip solution sending system, there can be mentioned for instance a system that is called a one pass type that is configured in such a manner that a specimen material solution passes through a reaction field only one time and a system that is called a reciprocation type that is configured in such a manner that a specimen material solution is reciprocated and passes through a reaction field in a repetitive manner (see Patent Documents 1 and 2 for instance).

FIG. 11 is a schematic view showing a conventional microchip solution sending system of a reciprocation type.

The conventional microchip solution sending system 100 of a reciprocation type is configured by a fine flow passage 110, the one side flow passage 132 and the other side flow passage 134 that are connected to the fine flow passage 110, and a micro pump 140 as shown in FIG. 11.

Inside the fine flow passage 110, a detection region 120 that is provided with a formed reaction field 122 is formed. On an edge part of one side of the fine flow passage 110, a first inflow outflow hole 112 is formed. The fine flow passage 110 and the one side flow passage 132 are connected to each other in such a manner that a solution can be flown through the first inflow outflow hole 112. In addition similarly, on an edge part of the other side of the fine flow passage 110, a second inflow outflow hole 114 is formed. The fine flow passage 110 and the other side flow passage 134 are connected to each other in such a manner that a solution can be flown through the second inflow outflow hole 114.

The micro pump 140 is connected to the upper edge part of the one side flow passage 132. By operating the micro pump 140, as shown in FIG. 12, the specimen material solution 136 that has been held in the one side flow passage 132 can be sent toward the fine flow passage 110 and the other side flow passage 134.

Moreover, the micro pump 140 can also send the specimen material solution 136 in a reverse direction of the solution sending direction described above by a suction of an air of the one side flow passage 132. In other words, as shown in FIG. 13, a solution can be sent from the one side flow passage 132 to the other side flow passage 134, and the specimen material solution 136 that has been held in the other side flow passage 134 can also be sent toward the fine flow passage 110 and the one side flow passage 132.

For the conventional microchip solution sending system 100 of a reciprocation type that is configured as described above, the specimen material solution 136 can be passed through the detection region 120 by reversing a solution sending direction of the micro pump 140 in a repetitive manner. By this configuration, an analyte of a desired amount can be captured at the reaction field 122 in a relatively efficient manner even in the case in which an amount of the specimen material solution 136 is small.

PRIOR ART DOCUMENTS

Patent Documents

[Patent Document 1]
Japanese Patent Application Laid-Open Publication No. 2006-90985
[Patent Document 2]
Japanese Patent Application Laid-Open Publication No. 2005-134372
[Patent Document 3]
International Patent Application Laid-Open Publication WO2011/027851

SUMMARY OF INVENTION

Problems to be Solved by the Invention

However, for the conventional microchip solution sending system 100 of a reciprocation type that is configured as described above, as shown in FIG. 12 and FIG. 13, in the case in which a solution amount of the specimen material solution 136 is small, after the specimen material solution 136 passes through the detection region 120, the detection region 120 has an exposure to an air. As a result, an active condition of an antibody that is fixed to the reaction field 122 is reduced, and a bubble of air is attached to an antibody, thereby reducing the reaction efficiency in some cases.

In particular, for the conventional microchip solution sending system in accordance with Patent Document 1 as described above, since an air is disposed in the specimen material solution 136 in a positive manner to send a solution, such a problem happens prominently.

Moreover, for the conventional microchip solution sending system in accordance with Patent Document 2 as described above, a solution sending direction of the micro pump 140 is switched in a unit of a predetermined period of time. By setting a time for switching a solution sending direction in a suitable manner, it is thought that an air can be prevented from entering the detection region 120. However, in the case in which a switching of a solution sending direction is tried to be controlled by setting a solution sending time as described above, an air inside the fine flow passage 110, the one side flow passage 132, and the other side flow passage 134 becomes a damper and it takes a long time to stop the specimen material solution 136 and to switch a solution sending direction. Therefore, a gap is generated for the timing for switching a solution sending direction and the timing for restarting the solution sending. As a result, a reciprocation position of the specimen material solution 136 is shifted from the detection region 120 by slow degrees in some cases.

In order to properly deal with such a problem, the present applicants have proposed a microchip solution sending system that is configured to switch a solution sending direction of the micro pump 140 in the case in which the specimen material solution 136 reaches to the predetermined solution level in which the solution level confirmation sensors 142 and 144 that are configured to confirm a solution level of the specimen material solution 136 are disposed to each of the one side flow passage 132 and the other side flow passage 134 as shown in FIG. 14 in the invention that has been applied in advance (Patent Document 3).

However, even for the conventional microchip solution sending system in accordance with Patent Document 3, in the case in which a solution amount of the specimen material solution 136 is small, the detection region 120 has an exposure to an air before a solution level of the specimen material solution 136 is detected by the solution level confirmation sensors 142 and 144 and a solution sending direction is switched. In order to solve this problem, it is necessary to set the solution level confirmation sensors 142 and 144 as close as possible to the detection region 120 of the fine flow passage 110. However, it is difficult to set the solution level confirmation sensors 142 and 144 to the fine flow passage 110 from the aspect of a setting space. In addition, in the case in which a microchip solution sending system is sued for the specimen material detection apparatus such as an SPR apparatus and an SPFS apparatus, the microchip solution sending system is in danger of preventing the specimen material from being detected.

The present invention was made in consideration of such a problem of a conventional technique, and an object of the present invention is to provide a microchip solution sending system capable of performing the solution sending of a specimen material solution in a reciprocating manner without the ingress of an air into a detection region even in the case in which a solution amount of the specimen material solution is small, whereby a specimen material can be detected with a small dispersion and with a high degree of accuracy.

Means for Solving the Problems

The present invention was made in order to solve the problems of the conventional art described above.

A microchip solution sending system in accordance with the present invention is characterized by comprising:

a flow passage assembly that is at least provided with a fine flow passage that is provided with a detection region including a formed reaction field to which an antibody that reacts with a specific antigen is fixed; and a micro pump that is connected to the flow passage assembly and that is configured to send a specimen material solution that includes the specific antigen in a reciprocating manner, wherein the specimen material solution that has been sent passes through the detection region in a repetitive manner in the case in which the micro pump sends the specimen material solution in a reciprocating manner, the microchip solution sending system comprising a solution sending amount measurement means that is configured to measure the amount of a solution that is sent from the micro pump, and a solution sending direction control means that is configured to reverse the solution sending direction of the micro pump, wherein in the case in which a specimen material solution is sent in a reciprocating manner by the micro pump in a state in which the flow passage assembly is filled with a specimen material solution and a partial zone of the flow passage assembly that includes the detection region is filled with a specimen material solution, in the case in which the amount of a solution that is sent from the micro pump is measured by the solution sending amount measurement means and the measured amount of the sent solution reaches a predetermined amount of the sent solution, the specimen material solution that has been sent passes through the detection region in a repetitive manner in a state in which the detection region is filled with the specimen material solution on a constant basis by reversing the solution sending direction by using the solution sending direction control means.

By the above configuration in which a solution sending direction can be controlled by the amount of a solution that is sent from the micro pump, the specimen material solution that has been sent passes through the detection region in a repetitive manner in a state in which the detection region is filled with the specimen material solution on a constant basis without setting a solution level confirmation sensor to the fine flow passage. Consequently, the microchip solution sending system can perform the reciprocated solution sending of a specimen material solution without the ingress of an air into a detection region even in the case in which an amount of the specimen material solution is small, whereby a specimen material can be detected with a small dispersion and with a high degree of accuracy.

For the above invention, the flow passage assembly is comprised of:

a fine flow passage that is provided with a first inflow outflow hole that is formed at the edge part of one side and a second inflow outflow hole that is formed at the edge part of the other side;

a one side flow passage that is connected to the fine flow passage via the first inflow outflow hole in such a manner that a solution can be passed through; and the other side flow passage that is connected to the fine flow passage via the second inflow outflow hole in such a manner that a solution can be passed through, and the micro pump is connected to the one side flow passage.

For the above invention in this case, it is preferable that the other side flow passage is a mixing part that is configured to store the specimen material solution that has passed through the detection region of the fine flow passage on a temporary basis and to stir the specimen material solution that has been stored.

In the case in which the other side flow passage is configured as a mixing part as described above, the microchip solution sending system can perform the reciprocated solution sending of a specimen material solution in a repetitive manner without reducing the reaction efficiency.

Moreover, it is preferable that the microchip solution sending system in accordance with the present invention is used for a surface plasmon resonance apparatus (an SPR apparatus) or a surface plasmon-field enhanced fluorescence spectroscopic measurement apparatus (an SPFS apparatus).

The microchip solution sending system in accordance with the present invention as described above can be used as a microchip solution sending system that is used for a surface plasmon resonance apparatus (an SPR apparatus) or a surface plasmon-field enhanced fluorescence spectroscopic measurement apparatus (an SPFS apparatus) in an appropriate manner in particular. By using the microchip solution sending system in accordance with the present invention for the SPR apparatus or the SPFS apparatus, the specimen material detection apparatus that is provided with the high reaction efficiency and a high accuracy with a small dispersion between individual pieces can be implemented as compared with an SPR apparatus or an SPFS apparatus that is provided with a conventional microchip solution sending system.

Advantageous Effects of Invention

By the microchip solution sending system in accordance with the present invention, for a microchip solution sending system of so-called a reciprocation type, a microchip solution sending system can be provided in which the microchip solution sending system can perform the reciprocated solution sending of a specimen material solution without the ingress of an air into a detection region even in the case in which a solution amount of the specimen material solution is small, whereby a specimen material can be detected with a small dispersion and with a high degree of accuracy.

BRIEF DESCRIPTION OF THE DRAWINGS

FIG. 1 is a schematic view for showing a microchip solution sending system in accordance with a first embodiment of the present invention.

FIG. 2 is a schematic view for illustrating a flow of a specimen material solution for a microchip solution sending system in accordance with a first embodiment of the present invention.

FIG. 3 is a schematic view for illustrating a flow of a specimen material solution for a microchip solution sending system in accordance with a first embodiment of the present invention.

FIG. 4 is a schematic view for showing a microchip solution sending system in accordance with a second embodiment of the present invention.

FIG. 5 is a schematic view for illustrating a flow of a specimen material solution for a microchip solution sending system in accordance with a second embodiment of the present invention.

FIG. 6 is a schematic view for illustrating a flow of a specimen material solution for a microchip solution sending system in accordance with a second embodiment of the present invention.

FIG. 7 is a schematic view for showing a microchip solution sending system in accordance with a third embodiment of the present invention.

FIG. 8 is a schematic view for illustrating a flow of a specimen material solution for a microchip solution sending system in accordance with a third embodiment of the present invention.

FIG. 9 is a schematic view for illustrating a flow of a specimen material solution for a microchip solution sending system in accordance with a third embodiment of the present invention.

FIG. 10 is a schematic view for showing a modified example of a microchip solution sending system in accordance with the present invention.

FIG. 11 is a schematic view showing a conventional microchip solution sending system of a reciprocation type.

FIG. 12 is a schematic view for illustrating a flow of a specimen material solution for a conventional microchip solution sending system of a reciprocation type.

FIG. 13 is a schematic view for illustrating a flow of a specimen material solution for a conventional microchip solution sending system of a reciprocation type.

FIG. 14 is a schematic view showing a conventional microchip solution sending system of another type.

DESCRIPTION OF EMBODIMENTS

An embodiment of the present invention will be described below in detail with reference to the drawings.

First Embodiment

FIG. 1 is a schematic view for showing a microchip solution sending system 1 in accordance with a first embodiment of the present invention.

As shown in FIG. 1, the microchip solution sending system 1 in accordance with the present invention is provided with a flow passage assembly A that is configured by a fine flow passage 10 that includes a detection region 20 and a one side flow passage 32 and the other side flow passage 34 that are connected to the both edge parts of the fine flow passage 10. A micro pump 40 is connected to the one side flow passage 32 of the flow passage assembly A.

As described later, in the case in which the flow passage assembly A is filled with a specimen material solution 36 and the specimen material solution 16 that has been filled with is sent in a reciprocating manner inside the flow passage assembly A by the micro pump 40, the specimen material solution 36 that has been sent can pass through the detection region 20 in a repetitive manner.

As shown in FIG. 1, the inside of the fine flow passage 10 is divided into the detection region 20, a one side flow passage part 24 that is formed continuously on one side of the detection region 20, and the other side flow passage part 26 that is formed continuously on the other side of the detection region 20.

Although a shape of a cross sectional surface and the dimensions of the fine flow passage 10 are not restricted in particular, the fine flow passage 10 is formed in a generally rectangular shape of a cross section in which a flow passage width is in the range of 0.5 mm to 3 mm and a flow passage height is in the range of 50 μm to 500 μm for instance. In addition, although a length of the flow passage of the fine flow passage 10 is not restricted in particular, the flow passage length is in the range of 2 mm to 30 mm, and in the range of 2 mm to 20 mm preferably for instance.

A detection region 20 is provided with a reaction field 22 that has been formed by fixing an antibody that reacts with a specific antigen in an idiosyncratic way to the bottom surface of the flow passage. In the case in which the specimen material solution 36 passes through the detection region 20, a specific antigen (analyte) that is included in the specimen material solution 36 reacts with an antibody that is fixed to the reaction field 22 in an idiosyncratic way and the specific antigen is captured by an antibody that is fixed to the reaction field 22.

A forming range of the reaction field 22 is appropriately configured in consideration of a shape of the fine flow passage 10 and an amount of an analyte that is supplied in such a manner that an analyte of a desired amount can be captured in an efficient manner, and the forming range of the reaction field 22 is not restricted in particular. In the present embodiment for instance, the reaction field 22 is formed along the whole width of the bottom surface of the fine flow passage 10, and a length in the direction of the flow passage is in the range of 1 mm to 3 mm.

As shown in FIG. 1, a first inflow outflow hole 12 is formed at an edge part on one side of a one side flow passage part 24 of the fine flow passage 10. In addition, a second inflow outflow hole 14 is formed at an edge part on the other side of the other side flow passage part 26 of the fine flow passage 10.

Although a shape of a cross sectional surface and the dimensions of the first inflow outflow hole 12 and the second inflow outflow hole 14 are not also restricted in particular, the first inflow outflow hole 12 and the second inflow outflow hole 14 are formed in a circular shape that is provided with a diameter that is almost equivalent to the flow passage width in the range of $\varphi 0.5$ mm to $\varphi 3$ mm of the fine flow passage 10 described above for instance.

As shown in FIG. 1, a one side flow passage 32 is connected to an edge part on one side of a one side flow passage part 24. The one side flow passage 32 and the fine flow passage 10 are connected to each other in such a manner that a solution can be flown through the first inflow outflow hole 12 described above.

The one side flow passage 32 is configured in such a manner that the specimen material solution 36 that is sent in a reciprocating manner can be flown through the one side flow passage 32, and the shape or the like is not restricted in particular. Moreover, the one side flow passage 32 can also be formed in an integrated manner with the fine flow passage 10, or can be connected to an object that has been formed individually from the fine flow passage 10. The one side flow passage 32 in accordance with the present embodiment is a pipette 32 that has been formed individually from the fine flow passage 10, and is configured in a detachable manner from the fine flow passage 10.

As shown in FIG. 1 moreover, the other side flow passage 34 is connected to an edge part on the other side of the other side flow passage part 26. The other side flow passage 34 and the fine flow passage 10 are connected to each other in such a manner that a solution can be flown through the second inflow outflow hole 14 described above.

The shape or the like of the other side flow passage 34 is not also restricted in particular. It is preferable that the other side flow passage 34 is formed as a mixing part 34 that is provided with a shape of a cross sectional surface that is larger than that of the second inflow outflow hole 14 described above. By this configuration, the specimen material solution 36 that has flown into the other side flow passage 34 (the mixing part 34) is stirred. Consequently, the specimen material solution 36 can be sent in a reciprocating manner in a repetitive manner without reducing the reaction efficiency for the detection region 20.

This is because the specimen material solution 36 is flown in the fine flow passage 10 in a laminar flow state, that is, a state in which the streamlines of fluids are generally parallel to each other on a constant basis. Consequently, in the case in which the mixing part 34 is not formed, the specimen material solution 36 of the same layer comes into contact with the reaction field 22 on a constant basis. As a result, only a part of the specimen material solution 36 contributes to a reaction. On the other hand, the mixing part 34 is formed in such a manner that a cross sectional shape of the mixing part 34 is larger than a cross sectional surface of the second inflow outflow hole 14. Consequently, in the case in which the specimen material solution 36 is flown into the mixing part 34, the specimen material solution 36 that is stored inside the mixing part 34 on a temporary basis is stirred due to a turbulence of a flow of the specimen material solution 36 that has been flown in a laminar flow state. Accordingly, even in the case in which the specimen material solution 36 passes on the detection region 20 in a repetitive manner, only the same layer does not come into contact with the reaction field 22, and most of the specimen material solution 36 contributes to a reaction on the reaction field 22.

A micro pump 40 is connected to an edge part on an opposite side of the fine flow passage 10 of the one side flow passage 32 described above. The micro pump 40 is a syringe pump that is configured to discharge and suck an air (or liquid) for the one side flow passage 32 for instance. In the case in which an air (or liquid) is discharged from the micro pump 40 to the pipette 32, the specimen material solution 36 can be sent from one side to the other side inside the flow passage assembly A as described above. Moreover, in the case in which an air (or liquid) of the pipette 32 is sucked by the micro pump 40, the specimen material solution 36 can be sent from the other side to one side inside the flow passage assembly A.

As shown in FIG. 1 moreover, a control part 48 is connected to the micro pump 40. The control part 48 is at least provided with a solution sending amount measurement means 42 that is configured to measure a solution sending amount of the micro pump 40 and a solution sending direction control means 44 that is configured to reverse a solution sending direction of the micro pump 40. In addition, the control part 48 is provided with a storage means 46 that is configured to store a solution sending amount Qp that is set in advance as a solution sending amount of the micro pump 40. A solution sending amount of the micro pump 40 is measured by the solution sending amount measurement means 42. In the case in which a solution sending amount that is measured reaches the solution sending amount Qp that has been stored into the storage means 46, the solution sending direction control means 44 issues a command to the micro pump 40 in order to switch an operation state of the micro pump 40 from a discharge to a suction (or from a suction to a discharge).

For the microchip solution sending system 1 in accordance with the present invention, an embodiment of the micro pump 40 is not restricted to the above described embodiment. For instance, even in the case in which two micro pumps: a micro pump capable of performing only a discharge and a micro pump capable of performing only a suction are prepared and the two micro pumps are connected to the both edge parts of the flow passage assembly A, respectively, the specimen material solution 36 can be sent in a reciprocating manner inside the flow passage assembly A.

In the next place, the following describes a flow of a specimen material solution 36 for a microchip solution sending system 1 in accordance with the present invention that is configured as described above based on FIG. 2 and FIG. 3.

FIG. 2 and FIG. 3 are the schematic views for illustrating a flow of a specimen material solution 36 for a microchip solution sending system 1 in accordance with a first embodiment of the present invention. An arrow in the figures indicates the solution sending direction of the specimen material solution 36.

In the state shown in FIG. 1, the fine flow passage 10 is filled with the specimen material solution 36 that has been held in the pipette 32, and an adjustment is carried out in such a manner that an air-liquid interface gl on the other side of the specimen material solution 36 that has been filled with is located on an interfacial boundary between the detection region 20 and the other side flow passage part 26. This filling operation is carried out by controlling the micro pump 40 manually for instance. As shown in FIG. 2(a) then, the initial state in which the detection region 20 is filled with the specimen material solution 36 is implemented.

In addition, a solution sending amount Qp (µl) that is set in advance as a solution sending amount of the micro pump 40 is stored into the storage means 46 of the control part 48 described above. In this case, in the case in which a total solution amount of the specimen material solution 36 that has been held in the pipette 32 described above is Q (µl) and a solution amount of the specimen material solution 36 that is corresponded to a volume of a space of the detection region 20 is Q1 (µl), a solution sending amount Qp that is set in advance in accordance with the present embodiment is obtained by the following formula (1).

$$Qp = Q - Q1 \quad (1)$$

In the next place, the micro pump 40 is operated from the initial state shown in FIG. 2(a), an air is discharged from the micro pump 40 to the pipette 32, and the specimen material solution 36 is sent from one side to the other side of the flow passage assembly A as shown in FIG. 2(b) and FIG. 2(c). In this case, a volume Vd (µl) of an air that is discharged from the micro pump 40 to the pipette 32 is measured by the solution sending amount measurement means 42.

In the case in which a volume Vd of an air that is discharged from the micro pump 40 to the pipette 32 reaches a solution sending amount Qp that has been set in advance, a command is issued from the solution sending direction control means 44 sending direction control means 44 to the micro pump 40, and the micro pump 40 is then operated to suck an air of the pipette 32 as that a solution sending amount Qp that has been set in advance has been sent.

In this case, in the state shown in FIG. 2(b) and FIG. 2(c), a part of the specimen material solution 36 that has passed through the detection region 20 is flown into the mixing part 34, and is stored and stirred on a temporary basis.

FIG. 3(a) shows a state immediately after an operation state of the micro pump 40 is switched from the discharge to the suction. In this state, an air-liquid interface gl on one side of the specimen material solution 36 is located on an interfacial boundary between the detection region 20 and the one side flow passage part 24, and the detection region 20 is filled with the specimen material solution 36.

In the next place, in the case in which the micro pump 40 is operated from the state shown in FIG. 3(a) in such a manner that an air of the pipette 32 is sucked, the specimen material solution 36 is sent from the other side to the one side of the flow passage assembly A as shown in FIG. 3(b) and FIG. 3(c). In this case, a volume Vs of an air that is sucked from the pipette 32 by the micro pump 40 is measured by the solution sending amount measurement means 42 described above.

In the case in which a volume Vs of an air that is sucked from the pipette 32 by the micro pump 40 reaches a solution sending amount Qp that has been set in advance, a command is issued from the solution sending direction control means 44 described above to the micro pump 40, and the micro pump 40 is then operated to discharge an air to the pipette 32 as that a solution sending amount Qp that has been set in advance has been sent.

FIG. 3(c) shows a state immediately before an operation state of the micro pump 40 is switched from the suction to the discharge. In this state, similarly to the initial state shown in FIG. 2(a) described above, an air-liquid interface gl on the other side of the specimen material solution 36 is located on an interfacial boundary between the detection region 20 and the other side flow passage part 26.

After that, by repeating the processes described above, the specimen material solution 36 is sent in a reciprocating manner inside the flow passage assembly A.

As described above, the microchip solution sending system 1 in accordance with the present invention is provided with a solution sending amount measurement means 42 that is configured to measure the amount of a solution that is sent from the micro pump 40 and a solution sending direction control means 44 that is configured to reverse the solution sending direction of the micro pump 40. In the case in which a volume Vd of an air that is discharged from the micro pump 40 (a volume Vs of an air that is sucked by the micro pump 40) reaches a solution sending amount Qp that has been set in advance as a solution sending amount of the micro pump 40, the solution sending direction is reversed in an automated way. Consequently, in the case in which a state shown in FIG. 2(a) is set as an initial state and a solution sending amount Qp that is set in advance is set as Q–Q1, that is obtained by subtracting a solution amount that is corresponded to a volume of a space of the detection region 20 from a total solution amount of the specimen material solution 36, the specimen material solution 36 that has been sent in a reciprocating manner passes through the detection region 20 in a repetitive manner in a state in which the detection region 20 is filled with the specimen material solution 36 on a constant basis.

Consequently, by the microchip solution sending system 1 in accordance with the present invention, the specimen material solution 36 can be sent in a reciprocating manner without the ingress of an air into a detection region 20 even in the case in which a solution amount of the specimen material solution 36 is small. Therefore, an active condition of an antibody that is fixed to the reaction field 22 can be prevented from being reduced, and a bubble of air can be prevented from being attached to an antibody, thereby preventing the reaction efficiency from being decreased.

In particular, by the microchip solution sending system 1 in accordance with the present invention, the specimen material solution 36 can be sent in a reciprocating manner in such a manner that an air-liquid interface gl (gl') of the specimen material solution 36 is located on a fine interfacial boundary of the detection region 20. Consequently, a small amount of the specimen material solution 36 can be applied to a reaction to the maximum extent possible.

In the case in which the microchip solution sending system 1 in accordance with the present invention is used for a surface plasmon resonance apparatus (an SPR apparatus) or a surface plasmon-field enhanced fluorescence spectroscopic measurement apparatus (an SPFS apparatus), an SPR apparatus or an SPFS apparatus that is provided with the high reaction efficiency and a high accuracy with a small dispersion between individual pieces can be implemented.

Second Embodiment

A microchip solution sending system 1 in accordance with a second embodiment of the present invention will be described below in detail with reference to FIG. 4 to FIG. 6.

FIG. 4 is a schematic view for showing a microchip solution sending system 1 in accordance with a second embodiment of the present invention.

For the first embodiment of the present invention described above, the description was made as that a volume Vd of an air that is discharged from the micro pump 40 (a volume Vs of an air that is sucked by the micro pump 40) is equivalent to a solution sending amount Qp of the specimen material solution 36 that has been set in advance. In other words, a compression rate of an air is not considered for the first embodiment of the present invention described above.

However, a volume of an air is varied depending on a temperature and a pressure. Consequently, in order to control a timing of a reverse of a solution sending direction of the specimen material solution 36 in a more precise manner, it is necessary to consider a compression rate (an expansion rate) of an air.

Therefore, the microchip solution sending system 1 in accordance with the present embodiment is provided with a temperature and pressure measurement means 50 that is configured to measure a temperature and a pressure inside the flow passage assembly A as shown in FIG. 4.

For the microchip solution sending system 1 in accordance with the present embodiment moreover, as shown in FIG. 4, the temperature and pressure measurement means 50 and the control part 48 are connected to each other, and a compression rate (an expansion rate) of an air under the conditions of a temperature and a pressure that have been measured is calculated in an automated way by the control part 48.

A volume Vd (Vs) of an air that has been measured by the solution sending amount measurement means 42 is then corrected by using a compression rate (an expansion rate) described above. In the case in which a volume V'd (V's) of an air after the correction reaches a solution sending amount Qp that has been set in advance, the solution sending direction is reversed by the solution sending direction control means 44.

For the microchip solution sending system 1 in accordance with the present embodiment that has been configured as described above, a more precise control of a solution sending amount can be easily carried out in consideration of a compression rate (an expansion rate) of an air.

For the embodiment as described above moreover, in the initial state shown in FIG. 2($a$), an air-liquid interface gl on the other side of the specimen material solution 36 is adjusted so as to be located on an interfacial boundary between the detection region 20 and the other side flow passage part 26. However, the microchip solution sending system 1 in accordance with the present invention is not restricted to the embodiment.

As shown in FIG. 5($a$) for instance, in the initial state before the reciprocated solution sending by the micro pump 40 is started, the flow passage assembly A can be filled with the specimen material solution 36 in such a manner that an air-liquid interface gl on the other side of the specimen material solution 36 is located at a distance L from the detection region 20.

In this case, in the case in which a total solution amount of the specimen material solution 36 is Q(µl), a solution amount of the specimen material solution 36 that is corresponded to a volume of a space of the detection region 20 is Q1(µl), and a solution amount of the specimen material solution 36 that is corresponded to a volume of a space for a region 28 of the fine flow passage that is corresponded to a distance L described above is Qr(µl), a solution sending amount Qp that is set in advance as a solution sending amount of the micro pump 40 can be set as indicated by the following formula (2).

$$Qp = Q - Q1 - Qr \qquad (2)$$

In the case in which an air-liquid interface gl on the other side of the specimen material solution 36 is located at a distance L from an interfacial boundary position between the detection region 20 and the other side flow passage part 26 in the initial state as described above, as shown in FIG. 5 and FIG. 6, in the case in which the specimen material solution 36 is sent in a reciprocating manner, an air-liquid interface gl (gl') is located at a distance L from the detection region 20, whereby an air can be prevented from entering into a detection region 20 with absolute certainty.

Third Embodiment

A microchip solution sending system 1 in accordance with a third embodiment of the present invention will be described below in detail with reference to FIG. 7 to FIG. 9.

FIG. 7 is a schematic view for showing a microchip solution sending system 1 in accordance with a third embodiment of the present invention.

For the present embodiment, as compared with the above described embodiment, the following points are different from the above described embodiment: the one side flow passage 32 is not connected to an edge part on one side of the fine flow passage 10, the fine flow passage 10 and the micro pump 40 are directly connected to each other, and a specimen material solution container 38 that is configured to contain the specimen material solution 36 is connected to the micro pump 40. The flow passage assembly A in this case is configured by the fine flow passage 10 and the mixing part 34.

For the microchip solution sending system 1 in accordance with the third embodiment, the specimen material solution 36 is sent in a reciprocating manner as shown in FIG. 8 and FIG. 9.

That is to say, in the case in which the micro pump 40 is operated in the initial state shown in FIG. 8($a$), the micro pump 40 sucks the specimen material solution 36 that has been contained in the specimen material solution container 38 and discharges the specimen material solution 36 to the fine flow passage 10. By this operation, the micro pump 40 sends the specimen material solution 36 from one side to the other side of the flow passage assembly A. In this case, a solution amount Qd of the specimen material solution 36 that is discharged from the micro pump 40 to the fine flow passage 10 is measured by the solution sending amount measurement means 42 described above.

After the all of the specimen material solution 36 that has been contained in the specimen material solution container 38 is discharged to the fine flow passage 10, as shown in FIG. 8($b$), the micro pump 40 discharges an air to the fine flow passage 10, thereby sending the specimen material solution 36 from one side to the other side of the flow passage assembly A. In this case moreover, a volume Vd of an air that is discharged from the micro pump 40 to the fine flow passage 10 is measured by the solution sending amount measurement means 42 described above.

In the case in which the total sum of a solution amount Qd of the specimen material solution 36 that is discharged from the micro pump 40 to the fine flow passage 10 and a volume Vd of an air that is discharged reaches a solution sending amount Qp that has been set in advance (a state shown in FIG. 8(c)), a command is issued from the solution sending direction control means 44 described above to the micro pump 40, and the micro pump 40 is then operated to suck an air of the fine flow passage 10 (a state shown in FIG. 9(a)).

In the states shown in FIG. 8(c) and FIG. 9(a), an air-liquid interface gl on the one side of the specimen material solution 36 is located on an interfacial boundary between the detection region 20 and the one side flow passage part 24 and the detection region 20 is filled with the specimen material solution 36.

In the case in which the micro pump 40 sucks an air of the one side flow passage part 24 of the fine flow passage 10, the specimen material solution 36 is sent from the other side to the one side of the flow passage assembly A as shown in FIG. 9(b). After the all of an air of the one side flow passage part 24 of the fine flow passage 10 is sucked, as shown in FIG. 9(c), the micro pump 40 directly sucks the specimen material solution 36 of the fine flow passage 10. In this case moreover, a volume Vs of an air and a solution amount Qs of the specimen material solution 36 that have been sucked by the micro pump 40 are measured by the solution sending amount measurement means 42 described above.

In the case in which the total sum of a volume Vs of an air and a solution amount Qs of the specimen material solution 36 that have been measured by the solution sending amount measurement means 42 reaches a solution sending amount Qp that has been set in advance, an air-liquid interface gl on the one side of the specimen material solution 36 is located on an interfacial boundary between the detection region 20 and the other side flow passage part 26 and the initial state shown in FIG. 8(a) described above is returned.

For the microchip solution sending system 1 in accordance with the present invention as described above, it is also possible that the one side flow passage 32 is not connected to an edge part on one side of the fine flow passage 10 and the fine flow passage 10 and the micro pump 40 are directly connected to each other.

For the microchip solution sending system 1 in accordance with the present invention moreover, in the case in which the specimen material solution 36 is sent in a reciprocating manner by the micro pump 40, the specimen material solution 36 can also be sent via a fluid such as an air. In addition, the specimen material solution 36 can also be sent in a reciprocating manner by directly discharging or sucking the specimen material solution 36.

Moreover, in the case in which the specimen material solution 36 is sent in a reciprocating manner via a fluid by the micro pump 40, as long as the fluid does not cause a change of the property of the specimen material solution 36, the fluid can also be a gas other than an air described above or can also be a liquid.

While the preferred embodiments in accordance with the present invention have been described above, the present invention is not restricted to the embodiments described above, and various changes, modifications, and functional additions can be thus made without departing from the scope of the present invention.

In the first to third embodiments described above for instance, the mixing part 34 as a second flow passage is connected to the edge part on the other side of the fine flow passage 10. Moreover, the mixing part 34 and the fine flow passage 10 are connected to each other via the second inflow outflow hole 14 in such a manner that a solution can be flown through.

However, the microchip solution sending system 1 in accordance with the present invention is not restricted to the embodiments described above. As shown in FIG. 10 for instance, in the case in which the other side flow passage part 26 of the fine flow passage 10 is provided with a capacity sufficient for holding the specimen material solution 36, it is not necessary that the mixing part 34 is connected to the edge part on the other side of the fine flow passage 10. In this case, the Flow passage assembly A is configured only by the fine flow passage 10.

REFERENCE SIGNS LIST

1: Microchip solution sending system
10: Fine flow passage
12: First inflow outflow hole
14: Second inflow outflow hole
20: Detection region
22: Reaction field
24: One side flow passage part
26: The other side flow passage part
28: Region
32: One side flow passage (pipette)
34: The other side flow passage (mixing part)
36: Specimen material solution
38: Specimen material solution container
40: Micro pump
42: Solution sending amount measurement means
44: Solution sending direction control means
46: Storage means
48: Control part
50: Temperature and pressure measurement means
100: Microchip solution sending system
110: Fine flow passage
112: First inflow outflow hole
114: Second inflow outflow hole
120: Detection region
122: Reaction field
132: One side flow passage
134: The other side flow passage
136: Specimen material solution
140: Micro pump
142: Solution level confirmation sensor
144: Solution level confirmation sensor
A: Flow passage assembly
gl and gl': Air-liquid interfaces

The invention claimed is:

1. A microchip solution sending system for use with a specimen material solution, the system comprising:
  a flow passage assembly comprising a fine flow passage comprising a detection region comprising a formed reaction field to which an antibody that reacts with a specific antigen is fixed; and
  a micro pump that is connected to the flow passage assembly and that is structured to send the specimen material solution that includes the specific antigen in a reciprocating manner,
  wherein the specimen material solution that has been sent passes through the detection region in a repetitive manner in the case in which the micro pump sends the specimen material solution in a reciprocating manner, the microchip solution sending system comprises a controller structured to measure the amount of a solution that is sent from the micro pump, and reverse the solution sending direction of the micro pump, the fine flow passage further comprises:
- a first inflow outflow hole that is formed at the edge part of one side of the fine flow passage;
- a second inflow outflow hole that is formed at the edge part of the other side of the fine flow passage;
- a one side flow passage part where the reaction field is not formed, the one side flow passage part connecting the first inflow outflow hole and the detection region; and
- an other side flow passage part where the reaction field is not formed, the other side flow passage part connecting the detection region and the second inflow outflow hole;
- wherein the one side flow passage part, the detection region, and the other side flow passage part are coaxial; and
- wherein a cross-sectional area of the fine flow passage is approximately equivalent along its length;

the flow passage assembly further comprises:
- a one side flow passage that is connected to the fine flow passage via the first inflow outflow hole in such a manner that a solution can be passed through; and
- an other side flow passage that is connected to the fine flow passage via the second inflow outflow hole in such a manner that a solution can be passed through, and the micro pump is connected to the one side flow passage, and
- the other side flow passage is a mixing part that is configured to store the specimen material solution that has passed through the detection region of the fine flow passage on a temporary basis and to stir the specimen material solution that has been stored, and wherein the controller is structured to measure the amount of a solution that is sent from the micro pump, and control the micro pump to reverse the solution sending direction of the specimen material solution when the measured amount of the sent solution reaches a predetermined amount of the sent solution, such that the specimen material solution is reciprocated between the detection region and the mixing part;

wherein the controller is structured to control the micro pump such that approximately all of the specimen material solution passes the detection region before the solution sending direction is reversed; and wherein at least one of the first inflow outflow hole and the second inflow outflow hole has a central axis nonparallel to a central axis of the fine flow passage.

2. The microchip solution sending system as defined in claim 1, wherein the microchip solution sending system is used for a surface plasmon resonance apparatus (an SPR apparatus) or a surface plasmon-field enhanced fluorescence spectroscopic measurement apparatus (an SPFS apparatus).

* * * * *